(12) United States Patent
Exline et al.

(10) Patent No.: US 6,551,282 B1
(45) Date of Patent: Apr. 22, 2003

(54) UNIVERSAL SEAL FOR USE WITH ENDOSCOPIC CANNULA

(75) Inventors: Donald D. Exline, Covington, KY (US); William A. Pierce, Dallas, TX (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 09/422,414

(22) Filed: Oct. 21, 1999

Related U.S. Application Data

(63) Continuation of application No. 09/027,754, filed on Feb. 23, 1998, now Pat. No. 5,989,224.

(51) Int. Cl.$^7$ .............................................. A61M 5/178
(52) U.S. Cl. .................................. 604/167.01; 604/256
(58) Field of Search ................................. 604/164, 167, 604/256, 264, 158, 164.01, 167.01–167.03, 167.06, 246, 247; 137/223, 225; 251/149.1, 5

(56) References Cited

U.S. PATENT DOCUMENTS

| | | |
|---|---|---|
| 3,421,509 A | 1/1969 | Fiore |
| 3,565,078 A | 2/1971 | Vailliancourt et al. |
| 3,853,127 A | 12/1974 | Spademan |
| 3,907,310 A | 9/1975 | Dufour |
| 3,994,287 A | 11/1976 | Turp et al. |
| 4,000,739 A | 1/1977 | Stevens |
| 4,112,932 A | 9/1978 | Chiulli |
| 4,173,350 A | 11/1979 | Sieghartner |
| 4,177,814 A | 12/1979 | Knepshield et al. |
| 4,177,997 A | 12/1979 | Cartwright |
| 4,240,335 A | 12/1980 | Stucka et al. |
| 4,240,411 A | 12/1980 | Hosono |
| 4,311,315 A | 1/1982 | Kronenberg |
| 4,334,688 A | 6/1982 | Spargo et al. |
| 4,338,689 A | 7/1982 | Zieg |
| 4,386,756 A | 6/1983 | Muchow |
| 4,387,879 A | 6/1983 | Tauschinski |
| 4,430,081 A | 2/1984 | Timmermans |
| 4,447,237 A | 5/1984 | Frisch et al. |
| 4,464,178 A | 8/1984 | Dalton |

(List continued on next page.)

FOREIGN PATENT DOCUMENTS

| | | |
|---|---|---|
| DE | 32 17 118 C1 | 8/1983 |
| EP | 0 696 459 B1 | 2/1946 |
| EP | 0 051 718 B1 | 5/1982 |
| EP | 0 113 520 A2 | 7/1984 |
| EP | 0 312 219 B1 | 4/1989 |
| EP | 0 316 096 | 5/1989 |
| GB | 1 482 857 | 8/1977 |
| WO | WO 93/04717 | 5/1992 |
| WO | WO 98/53865 | 5/1998 |
| WO | WO 99/52577 | 3/1999 |

*Primary Examiner*—Julian W. Woo

(57) ABSTRACT

A universal seal is shown with orbital movement of a center opening for use in endoscopic surgery. A two part seal housing encloses the universal seal in an annulus surrounding an insertion port. The outer periphery of the universal seal is clamped between the two parts at the outer edge of the annulus. An inner ring of the universal seal is free to move from side-to-side inside the annulus while maintaining rubbing contact with the upper and lower surfaces of the annuluses for vertical support. The seal housing and universal seal are mounted on a proximal end of a cannula which allows access therethrough for the endoscopic surgery. The center opening of the universal seal is in general alignment with the insertion port of the seal housing, but the center opening and inner ring may move from side to side when medical instruments are inserted through the insertion port, the center opening, and the cannula and moved from side to side.

21 Claims, 3 Drawing Sheets

U.S. PATENT DOCUMENTS

| | | |
|---|---|---|
| 4,553,760 A | 11/1985 | Reed et al. |
| 4,588,195 A | 5/1986 | Antonini et al. |
| 4,601,710 A | 7/1986 | Moll |
| 4,626,245 A | 12/1986 | Weinstein |
| 4,641,842 A | 2/1987 | Kataoka |
| 4,654,030 A | 3/1987 | Moll et al. |
| 4,655,752 A | 4/1987 | Honkanen et al. |
| 4,673,393 A | 6/1987 | Suzuki et al. |
| 4,705,511 A | 11/1987 | Kocak |
| 4,715,360 A | 12/1987 | Akui et al. |
| 4,723,550 A | 2/1988 | Bales et al. |
| 4,758,225 A | 7/1988 | Cox et al. |
| 4,842,591 A | 6/1989 | Luther |
| 4,844,483 A | 7/1989 | Iijima et al. |
| 4,844,484 A | 7/1989 | Antonini et al. |
| 4,857,062 A | 8/1989 | Russell |
| 4,869,717 A | 9/1989 | Adair |
| 4,874,378 A | 10/1989 | Hillstead |
| 4,889,349 A | 12/1989 | Muller |
| 4,909,798 A | 3/1990 | Fleischhacker et al. |
| 4,917,668 A | 4/1990 | Haindl |
| 4,929,235 A | 5/1990 | Merry et al. |
| 4,932,633 A | 6/1990 | Johnson et al. |
| 4,943,280 A | 7/1990 | Lander |
| 4,960,412 A | 10/1990 | Fink |
| 4,966,588 A | 10/1990 | Rayman et al. |
| 4,998,740 A | 3/1991 | Tellier |
| 5,000,745 A | 3/1991 | Guest et al. |
| 5,002,557 A | 3/1991 | Hasson |
| 5,015,000 A | 5/1991 | Perini |
| 5,038,756 A | 8/1991 | Kepley |
| 5,041,095 A | 8/1991 | Littrell |
| 5,053,014 A | 10/1991 | Van Heugten |
| 5,053,016 A | 10/1991 | Lander |
| 5,073,169 A | 12/1991 | Raiken |
| 5,104,383 A | 4/1992 | Schichman |
| 5,127,626 A | 7/1992 | Hilal et al. |
| 5,137,520 A | 8/1992 | Maxson et al. |
| 5,167,636 A | 12/1992 | Clement |
| 5,180,373 A | 1/1993 | Green et al. |
| 5,197,955 A | 3/1993 | Stephens et al. |
| 5,201,714 A | 4/1993 | Gentelia et al. |
| 5,209,736 A | 5/1993 | Stephens et al. |
| 5,209,737 A | 5/1993 | Ritchart et al. |
| 5,221,264 A | 6/1993 | Wilk et al. |
| 5,226,891 A | 7/1993 | Bushatz et al. |
| 5,242,412 A | 9/1993 | Blake, III |
| 5,290,304 A | 3/1994 | Storace |
| 5,299,813 A | 4/1994 | McKenna |
| 5,300,036 A | 4/1994 | Mueller et al. |
| 5,308,336 A | 5/1994 | Hart et al. |
| 5,320,611 A | 6/1994 | Bonutti et al. |
| 5,342,315 A | 8/1994 | Rowe et al. |
| 5,354,280 A | 10/1994 | Haber et al. |
| 5,380,288 A | 1/1995 | Hart et al. |
| 5,385,553 A | 1/1995 | Hart et al. |
| 5,391,153 A | 2/1995 | Haber et al. |
| 5,395,342 A | 3/1995 | Yoon |
| 5,400,586 A | 3/1995 | Bagepalli et al. |
| 5,407,433 A | 4/1995 | Loomas |
| 5,411,483 A | 5/1995 | Loomas et al. |
| 5,429,609 A | 7/1995 | Yoon |
| 5,439,455 A | 8/1995 | Kieturakis et al. |
| 5,443,452 A | 8/1995 | Hart et al. |
| 5,485,553 A | 1/1996 | Kovalick et al. |
| 5,496,280 A | 3/1996 | Vandenbroek et al. |
| 5,512,053 A | 4/1996 | Pearson et al. |
| 5,545,142 A | 8/1996 | Stephens et al. |
| 5,554,124 A | 9/1996 | Alvarado |
| 5,568,931 A | 10/1996 | Tseng et al. |
| 5,584,850 A | 12/1996 | Hart et al. |
| 5,628,732 A | 5/1997 | Antoon, Jr. et al. |
| 5,634,908 A | 6/1997 | Loomas |
| 5,634,911 A * | 6/1997 | Hermann et al. ............ 604/256 |
| 5,634,937 A | 6/1997 | Mollenauer et al. |
| 5,643,227 A | 7/1997 | Stevens |
| 5,643,301 A | 7/1997 | Mollenauer |
| 5,709,664 A | 1/1998 | Vandenbroek et al. |
| 5,743,884 A | 4/1998 | Hasson et al. |
| 5,752,938 A | 5/1998 | Flatland et al. |
| 5,782,812 A | 7/1998 | Hart et al. |
| 5,782,817 A * | 7/1998 | Franzel et al. .............. 604/256 |
| 5,792,113 A | 8/1998 | Kramer et al. |
| 5,820,600 A * | 10/1998 | Carlson et al. ............. 604/167 |
| 5,827,228 A | 10/1998 | Rowe |
| 5,857,999 A | 1/1999 | Quick et al. |
| 5,868,714 A | 2/1999 | Danks |
| 5,944,320 A | 8/1999 | Werner et al. |
| 5,989,224 A | 11/1999 | Exline et al. |
| 5,997,515 A | 12/1999 | De la Torre et al. |
| 6,042,119 A | 3/2000 | Bagepalli et al. |
| RE36,702 E | 5/2000 | Green et al. |
| 6,228,061 B1 | 5/2001 | Flatland et al. |
| 6,276,661 B1 * | 8/2001 | Laird .......................... 604/256 |

\* cited by examiner

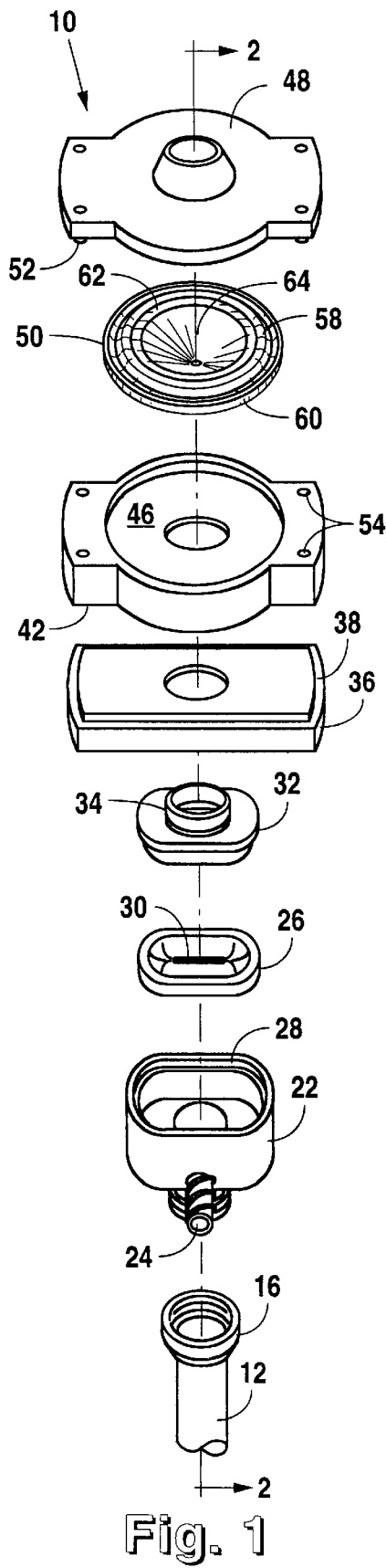
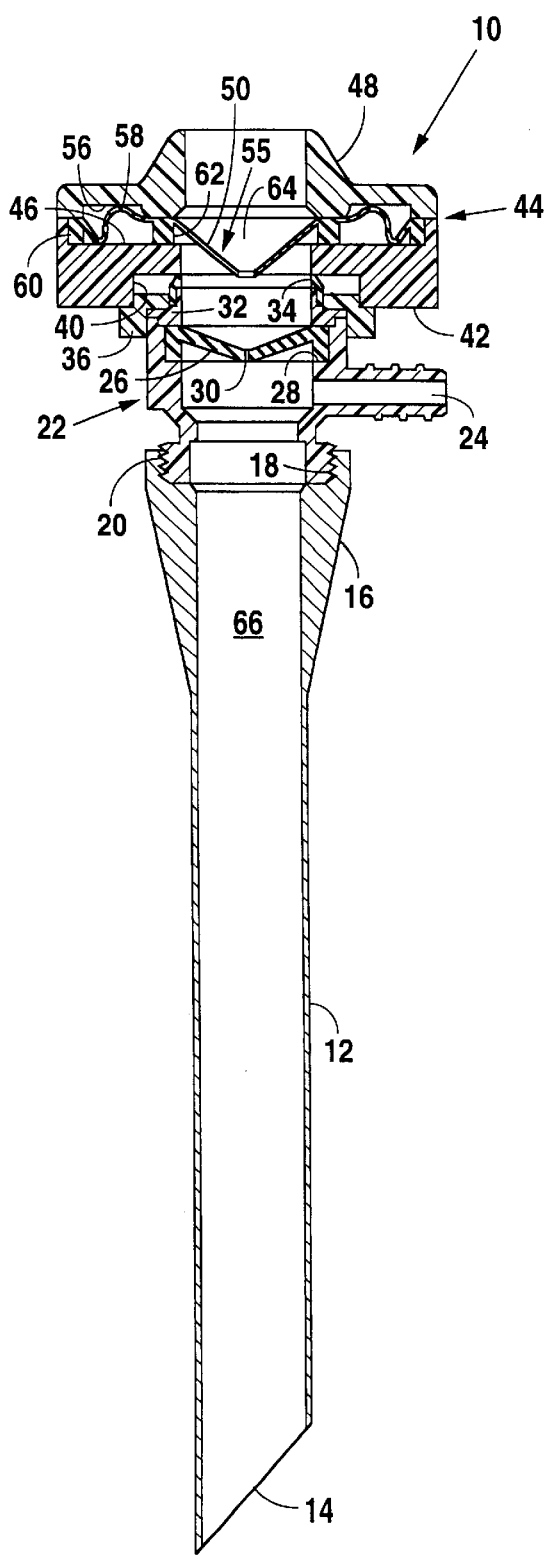

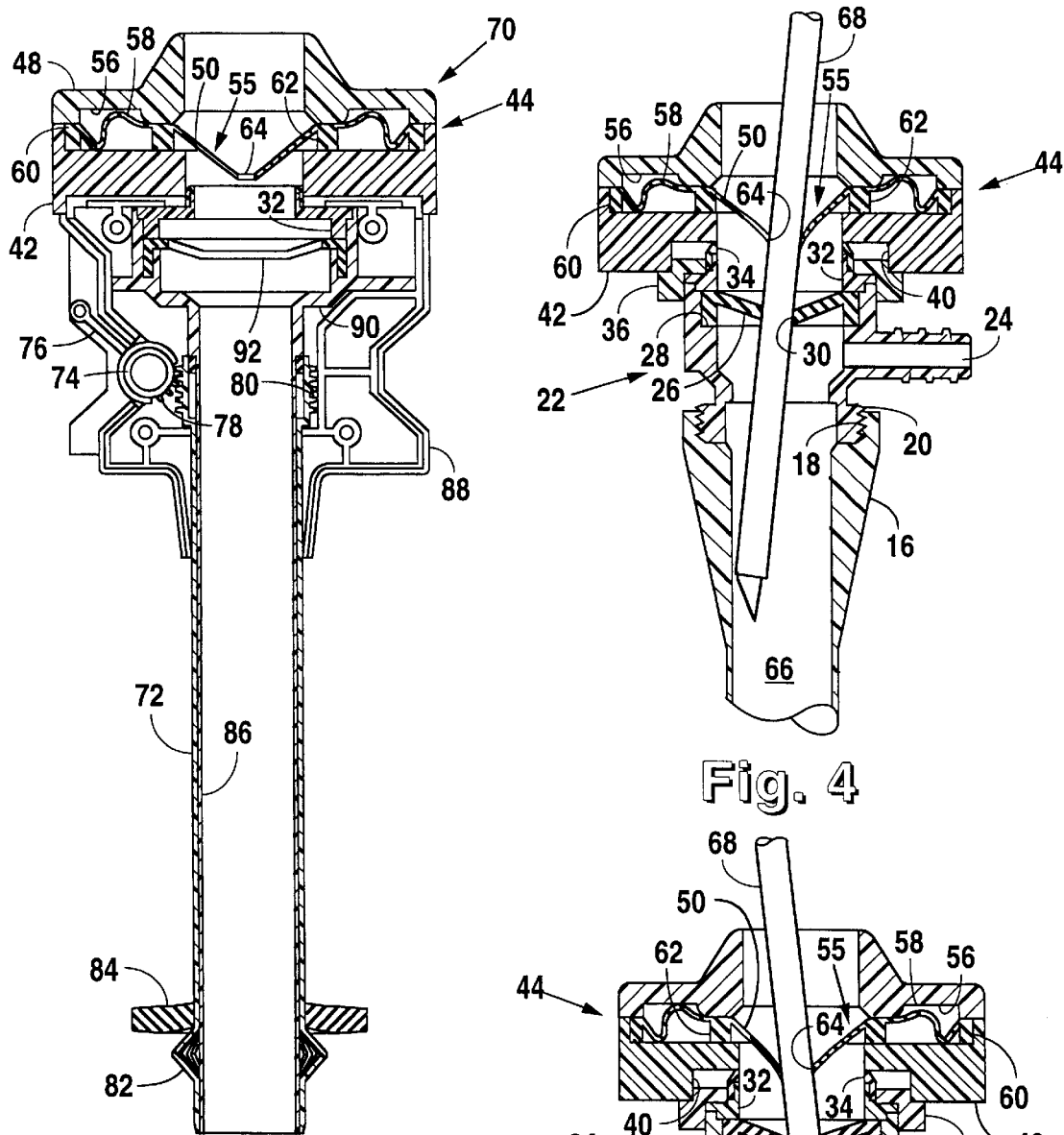
Fig. 3
Fig. 4
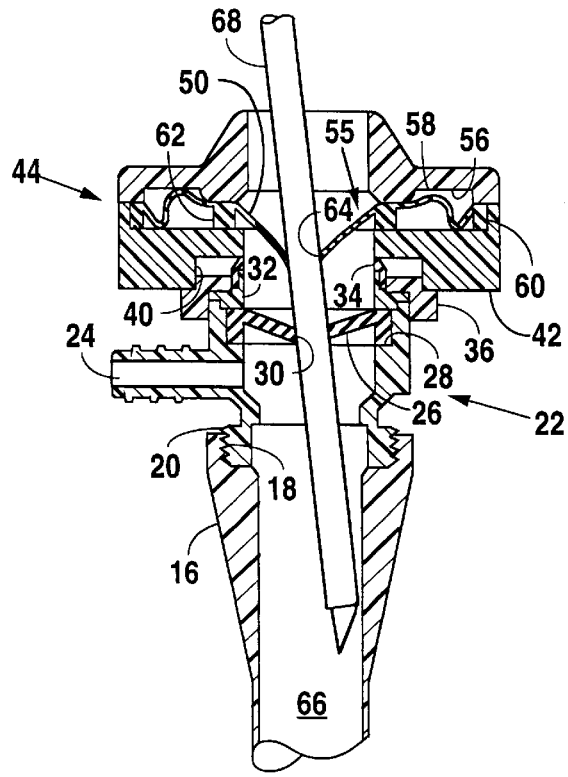
Fig. 5

UNIVERSAL SEAL FOR USE WITH ENDOSCOPIC CANNULA

This application is a Continuation of prior application Ser. No. 09/027,754 filed on Feb. 23, 1998, now U.S. Pat. No. 5,989,224.

FIELD OF THE INVENTION

The present invention relates generally to seals for use in endoscopic surgery and, more particularly, to a universal seal that seals against different sizes of medical instruments being inserted through a cannula into the body while maintaining insufflation pressure, yet still allowing for side to side motion of the medical instruments.

BACKGROUND OF THE INVENTION

As modern technology has developed, new surgical innovations have followed the technology. One of the techniques of modern surgery that has rapidly grown in the last decade is the use of small openings in the body through which access to the internal organs is obtained. While many different titles to describe this technique have been used, probably the more common titles are laparoscopic surgery or endoscopic surgery. Other people prefer more descriptive titles such as telescopic surgery or minimally invasive surgery. This entire area of surgical techniques probably developed the most in laparoscopic cholecystectomy, which is used to remove gall stones.

For the present application, because the most commonly used and comprehensive term is endoscopic surgery, the term endoscopic surgery will be used in this application to refer collectively to all of these types of surgery. However, it should be realized that other terms can be used to describe the surgical technique.

In endoscopic surgery, a small cut is made in the skin and a sharpened cannula or spike is then inserted through the fascia into a body opening such as the abdominal cavity. After removal of the spike from the cannula, the cannula will then allow access to the body opening such as the abdominal cavity.

Typically, a gas is inserted through the cannula to insufflate the body opening. Once the first opening is made, a camera lens on the end of a fiber optic cable can be inserted through the cannula that will allow the monitoring of the internal parts of the body cavity. It is extremely important that the body organs not be damaged when inserting any cannulas, spikes, or trocars into the body.

After access to the body opening is obtained by the insertion of the cannula, it is also important to maintain a seal along the central opening of the cannula. If not, the gas used for the insufflation of the body cavity will rapidly escape and it will be difficult to maintain a sufficient cavity opening for the endoscopic surgery.

In the past, various types of seals have been developed to seal the upper part of the cannula opening. An example is shown in U.S. Pat. No. 5,512,053, which patent is owned by the same assignee as the present application. U.S. Pat. No. 5,512,053 provides a lip seal to maintain the insufflation gas in the body cavity. However, once a medical instrument is inserted through the lip seal, the gas can leak around the medical instrument and escape into the atmosphere. To provide a back up, a second sliding seal with different size apertures has been provided to engage the medical instrument being inserted into the cannula and through the lip seal. Medical instruments vary in size, and the medical instruments will be moved form side to side during use in endoscopic surgery. This side to side motion causes leakage of the gas around the medical instruments. Some type of seal is needed that will seal around medical instruments of varying sizes and, at the same time, allow for lateral or side to side movement of the medical instrument during endoscopic surgery.

Also, it is important that the seal have a memory to return to its original position after periods of use. In other words, if the doctor during the operation is moving the medical instrument to one side, there should be a continual force trying to urge the medical instrument back to the center of the cannula opening.

To remedy the problem of different size medical instruments being inserted through the cannula, U.S. Pat. No. 4,112,932 shows a laparoscopic cannula that has a rotating seal where different size openings can be selected depending upon the size of instrument being inserted into the cannula. While this is effective to some degree, it does not allow for side to side movement of the medical instrument and it does not allow for the rapid exchange of medical devices without also rotating or spinning the seal.

A common seal that is in use today to seal surgical instruments such as cannulas, trocars, or similar devices is shown in U.S. Pat. No. 5,407,433 to Loomas. The Loomas patent and its related patents allows some side to side movement of the medical instruments, but has a rigid internal ring on the seal that limits its effectiveness. The rigid internal ring does not allow the seal to make a sealing relationship with the medical instrument as well as the present invention. The inflexible nature of the internal ring does not provide as effective an urging force against the medical instrument to return the medical instrument to the center of the cannula. The Loomas seal is also much more complicated and expensive to manufacture than the present universal seal and does not provide as effective sealing as the present invention.

To overcome this problem of accommodating different sizes of medical instruments and to allow for side to side movement, many other United States patents have been issued to seal surgical instruments such as cannulas or trocars. Another example is U.S Pat. No. 5,342,315 issued to Rowe, which has a whole collection of different types of seals. Each of these seals is much more complicated and expensive to manufacture than the present invention and still is not as effective. The Rowe patent shows all types of reinforcing ribs and slots being cut in the seal, none of which are necessary with the present invention.

Other patents refer to their seal as a "universal seal" such as U.S. Pat. No. 5,628,732 to Antoon or U.S. Pat. No. 5,350,364 to Stephens. Again, both of these patents are much more complicated, expensive, and do not do the job of the present universal seal. Applicants, who are very familiar with the industry, does not know of any other seal that is as economical and inexpensive to manufacture as the present universal seal, but is as effective in allowing different size instrument to be inserted through a cannula and allowing side to side movement of the medical instrument, yet still maintaining air tight contact to hold the insufflation gas inside the body cavity. The need exists for a universal type of seal that can be used for any cannula or trocar device through which access is obtained to body cavities for the purpose of performing endoscopic surgery, particularly while sealing against the surgical instruments being inserted through the cannulas or trocars into the body.

SUMMARY OF THE INVENTION

It is an object of the present invention to provide a universal seal.

It is another object of the present invention to provide a seal for cannulas or other devices used in endoscopic surgery.

It is still another object of the present invention to provide for a universal seal that can be used with cannulas or trocars, which universal seal allows for side to side movement with different size surgical instruments when inserted therethrough, yet still maintaining an air tight seal to hold the insufflation gas inside the body.

It is yet another object of the present invention to provide a cannula with an improved seal for sealing against the surgical instruments being inserted through the cannula into the body cavity while still urging the surgical instrument and the seal back to the center of the cannula due to the memory of the elastomeric material.

It is still another object of the present invention to provide a universal seal that can seal against medical instruments of different diameters as they are inserted through a cannula or trocar during endoscopic surgery and still maintain the seal during side to side movement of the medical instrument.

The universal seal is shown in a preferred embodiment in combination with a reusable cannula. The reusable cannula is made from a metal material and is connected to a lip seal housing for a lip seal. An insufflation port connects through the lip seal housing into the central passage of the reusable cannula below the lip seal. Above the lip seal housing is an adapter so that different devices or seals may be attached to the lip seal housing.

Above the adapter is a universal housing, which maintains a universal seal between a top and bottom portion of the universal seal housing. The top and bottom portions form an annulus therebetween that surrounds an insertion port in the universal seal housing. An outer ring of the universal seal is compressed at the outer edge of the annulus between the bottom and top portions of the universal seal housing. An inner ring of the universal seal is free to move back and forth inside of the annulus while maintaining rubbing contact with the top and bottom portions of the universal seal housing which forms the annulus. A small opening is in the center of the universal seal.

Because the universal seal is made from elastomeric material, as medical instruments of different diameters are inserted through the insertion port into the small opening of the universal seal, the small opening in the universal seal will expand to accommodate the different size medical instruments up to a predetermined limit. If the medical instrument moves from side to side, the center ring of the universal seal will deform and move inside of the annulus to allow for side to side movement of the medical instrument while still maintaining contact with the medical instrument. The universal seal will have a tendency to self center that is caused by a combination of (a) memory of the elastomeric material, (b) gas pressure on the underside of the universal seal, and (c) geometry of the universal seal. This combination creates what could be called an annular spring.

Several different embodiments of the universal seal are shown. Also, the universal seal with the seal,housing may be attached to other types of medical devices such as trocars for allowing entry into the body for endoscopic surgery.

BRIEF DESCRIPTION OF THE DRAWINGS

FIG. 1 is an exploded perspective view of the present invention being used with a reusable cannula.

FIG. 2 is a cross-sectional view of FIG. 1, when assembled, taken along section lines 2—2.

FIG. 3 is an elevated cross-sectional view of the present invention being used with a locking trocar.

FIG. 4 is a partial cross-sectional view of a cannula utilizing the present invention with the medical instrument being moved to the right side.

FIG. 5 is a partial cross-sectional view of a cannula utilizing the present invention with the medical instrument being moved to the left side.

DESCRIPTION OF THE PREFERRED EMBODIMENT

Figure 6:
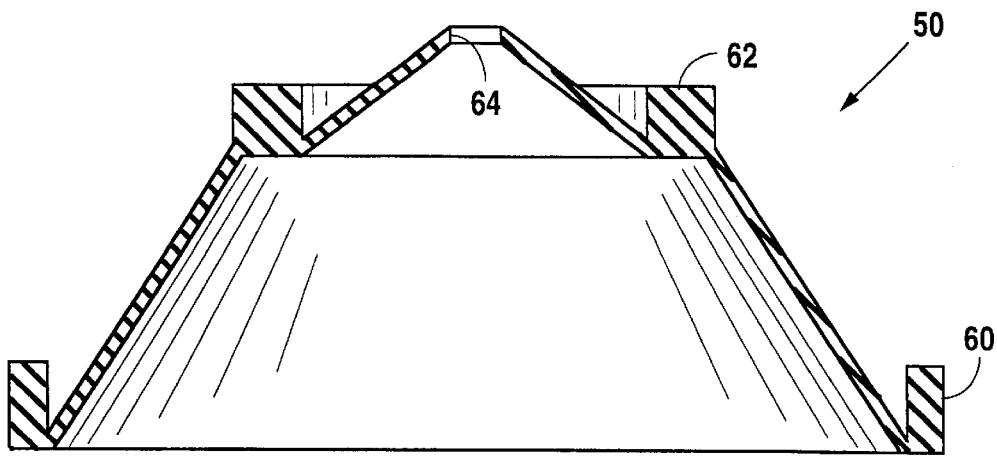
FIG. 6 is an enlarged cross-sectional view of the universal seal as manufactured.

Referring to FIGS. 1 and 2 in combination, the universal seal of the present invention is shown in a reusable cannula referred to generally by reference number 10. The cannula 12 has a slanted cut lower distal end 14 from which a spike or similar instrument (not shown) may extend.

An enlarged upper portion 16 of the cannula 12 has upper internal threads 18 for threadably connecting to lower threads 20 of a lip seal body 22.

The lip seal body 22 has a port 24 through which insufflation gas is inserted. The insufflation gas 30 is directed downward through the cannula 12 into the body of the patient.

A lip seal 26 is located on an internal shoulder 28 of the lip seal body 22. A slot 30 is cut in the lip seal 26, which slot 30 may be opened upon the insertion of medical instruments.

A snap cap 32 snaps onto the upper portion of the lip seal body 22 to securely hold the lip seal 26 in position. The snap cap 32 may be held to the lip seal body by any conventional means such as snap posts (not shown). Around the upper part of the snap cap 32 is an elastomeric ring 34 that provides a good fit with the adapter 36. The adapter 36, also called a Chiulli adapter, is used so that access can be obtained to the cannula for the removal of body tissue. It is important not to have to go through any further seals in reaching into the body and removing irregular objects.

While the adapter 36 can be of any particular configuration, in the present preferred embodiment, it is of an elongated shape and has a mating shoulder/edge 38. The mating shoulder/edge 38 is received into a mating cavity 40 formed in the bottom 42 of the universal seal housing 44. The connection between the adapter 46 and the bottom 42 of the universal seal housing 44 is an air tight seal that will not allow insufflation gas to escape therethrough. A circular opening 46 is in the top of the bottom 42 of the universal seal housing 44. The top 48 of the universal seal housing 44 connects to the bottom 42 by any conventional means. Therebetween is located the universal seal 50, which will be described in more detail subsequently. In this preferred embodiment, the bottom 42 and the top 48 are held together by snap. posts 52 snapping into holes 54 to hold the universal seal housing 44 together.

Referring to FIG. 2, it can be seen that the top portion 48 has an angular undercut 56 formed therein that is just above the circular opening 46 in the bottom 42 of the universal seal housing 44. The angular undercut 56 with the circular opening 46 forms an annulus in which a roll or bellows 58 of the universal seal 50 is located. An outer ring 60 of the universal seal 50 is pressed between the bottom 42 and the top 48 in a solid sealing relationship. The outer ring 60 is held very securely in place.

An inner ring 62 of the universal seal 50 is located inside of the roll or bellows 58. The inner ring 62 is free to slide back and forth in sliding contact with the bottom side of the top 48 or the circular opening 46 of the bottom 42 of the universal seal housing 44. In the middle of the universal seal 50 is located an opening 64 through which medical instruments (not shown) may be inserted. The opening 64 is in alignment with the center of the central passage 66 which extends through the universal seal housing 44, adapter 36, snap cap 32, lip seal body 22, and cannula 12.

The inner ring 62 prevents the universal seal 50 from being pushed into tthe central passage 66 when inserting a large diameter instrument, or from being pulled into the central passage 66 when removing a large diameter instrument.

Referring now to FIGS. 4 and 5 in combination, an elevated partial cross-sectional view of the reusable cannula with the universal seal 50 is shown. A medical instrument 68 is inserted through the opening 64 of the universal seal 50. As the medical instrument 68 is moved to the right hand side as illustrated in FIG. 4, the inner ring 62, while still maintaining sliding contact with the top portion 48 and the bottom portion 42, moves to the right as the opening 64 moves to the right. The roll or bellows 58 of the universal seal 50 compresses in the right hand direction and elongates in the left hand direction. Also, the inner ring 62 being deformable may deform as the medical instrument 68 moves to the right. The medical instrument 68 will extend down through the opening 64 of the universal seal 50 and through the slot 30 in the lip seal 26. While it is not shown in the drawings, the slot 30 has a tendency to allow insufflation gas to escape on either end of the slot adjacent to the medical instrument 68. Therefore, it is important that the universal seal 50 have a good sealing relationship with the medical instrument 68.

As the medical instrument 68 moves to the left as shown in FIG. 5, the opening 64 moves to the left. Likewise, the inner ring 62 moves to the left as well. Again, the roll or bellows 58 on the universal seal 50 tends to compress to the left and expand to the right. Again, a good sealing relationship is maintained with the medical instrument 68.

As can be seen in FIGS. 2, 3, 4 and 5, the universal seal 50 has a downward conical shape 55 that allows for ease of insertion of a medical instrument without tearing or damage. Gas pressure against the downward conical shape 55 also helps insure an air-tight seal against a medical instrument.

While in the present view, the medical instrument is shown as a surgical cutting device, any other type of medical instrument may be inserted such as surgical devices, lens on the end of fiber optic links, clip appliers, just to name a few of the medical instruments.

Referring to FIG. 6, the universal seal 50 is shown as it comes out of the mold and as it would normally appear. In this enlarged view, the configuration of the outer ring 60, inner ring 62, and opening 64 is clearly visible.

Figure 7:
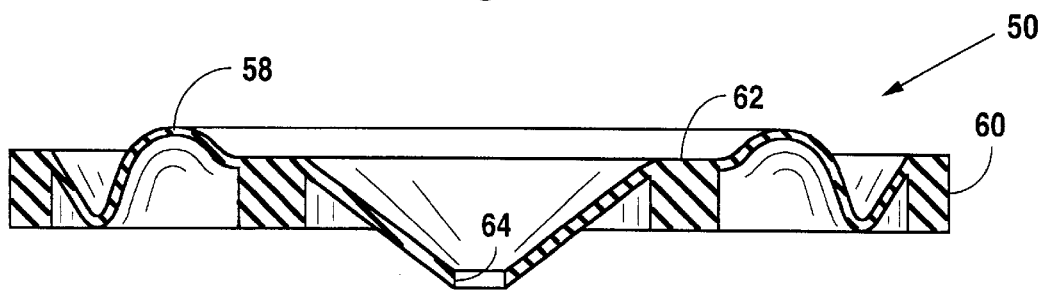
FIG. 7 is a cross-sectional view of the universal seal in its normal position when installed in the universal seal housing.

As the universal seal 50 is installed in the universal seal housing 44, it will assume the configuration as shown in FIG. 7 with the roll 58 as clearly shown. The outer ring 60 may be compressed when installed. Otherwise, FIG. 7 is an enlarged representation of the view of the universal seal 50 when in operation.

Referring to FIG. 3, an alternative use for the universal seal 50 is shown in a trocar arrangement, the trocar being generally referred to with reference number 70. The trocar 70 as shown in FIG. 3 is a locking trocar that has a molly bolt type of arrangement for an outer cylinder 72. A molly bolt 74 has a lever 76 that is pivoted up or down, which causes the gear 78 on the molly bolt to pivot. The gears 78 of the molly bolt engages the corresponding outer cylinder gears 80 which are on the top of the outer cylinder 72.

The outer cylinder 72 moves up and down as the lever 76 is moved down and up. When the outer cylinder 72 is moved down, expandable members 82 extend outward as shown in FIG. 3. In that manner, the outer skin or fascia of the body in which the trocar 70 is being inserted is maintained solidly in position between the retaining ring 84 and the expandable members 82. If the outer cylinder 72 is moved up by pivoting the lever 76 down, the expandable members 82 will close so that the outer cylinder 72 appears as an ordinary cylinder.

The outer cylinder 72 is riding on an inner cylinder 86 which is securely mounted into position at the top by housing 88. The housing 88 may be made from two pieces of injection molded plastic that are fused or snapped together. Inside of the housing 88 is a lip seal housing 90 in which the lip seal 92 is located.

Above the housing 88 and the lip seal housing 90 is located the universal seal 50 and universal seal housing 44 as previously described in connection with FIGS. 1 and 2. The configuration of the universal seal 50 and universal seal housing 44 is the same as previously described; therefore, it will not be described again in connection with the trocar arrangement of FIG. 3.

Referring now to FIGS. 6 and 7 in combination, FIG. 6 shows the universal seal 50 as it comes out of the mold in which the elastomeric material forming the universal seal 50 is cast. When the universal seal 50 is put in the universal seal housing 44, it will be pushed down as is illustrated in FIG. 7. The inner ring 62 pushes down as is pictorially illustrated in FIGS. 2 and 5.

Figure 8:
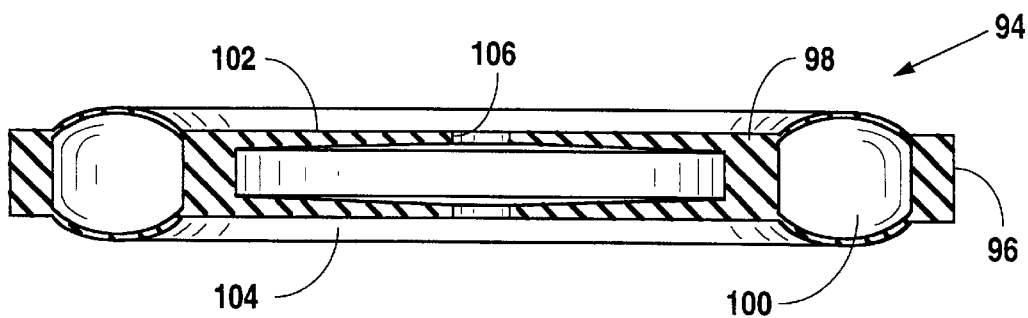
FIG. 8 is an alternative embodiment of the universal seal of the present invention.

Referring now to FIG. 8, a modified universal seal 94 is shown which can still fit in the universal seal housing 44. The modified universal seal 94 has an outer ring 96 which is secured in position between the bottom 42 and top 48 of the universal seal housing 44. An inner ring 98 is connected by an air bladder 100 with outer ring 96. Extending inward from inner ring 98 is upper membrane 102 and lower membrane 104, both of which have a center opening 106.

The inner ring 98 will be in rubbing contact with the bottom 42 and top 48 of the universal seal housing 44. The modified universal seal 94 will flex generally in the same way as the universal seal 50 described in the preferred embodiment with the inner ring 98 flexing as the medical instrument inserted therethrough may move from side to side. Also, the modified universal seal 94 will accommodate varying sizes of medical instruments being inserted.

Figure 9:
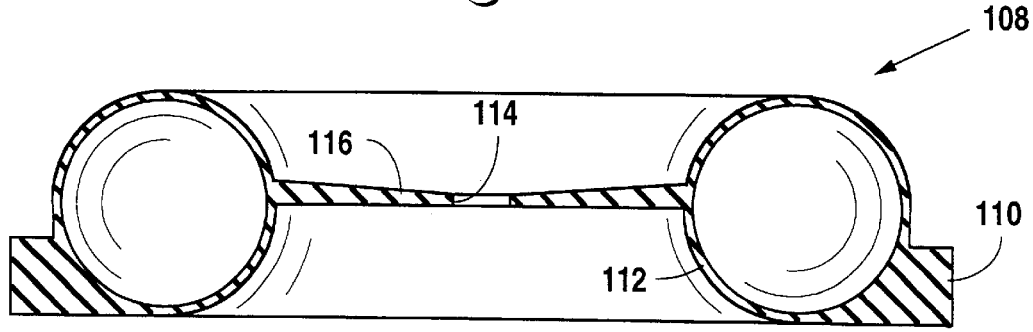
FIG. 9 is another alternative embodiment of the universal seal of the present invention.

Referring to FIG. 9; a further modification of the universal seal is shown and is referred to generally by reference numeral 108. The modified universal seal 108 still has an outer ring 110 that is securely clamped into position by a universal seal housing 44. However, in the modified version shown in FIG. 9, the inner ring has been replaced entirely by an annular air bladder 112. The outer portion of the annular air bladder 112 is formed integral with the outer ring 110. Extending inward from the annular air bladder 112 to a central opening 114 is the center membrane 116. Again, as described with the prior embodiments, the annular air bladder 112 will allow for side to side movement of the medical instruments being inserted through the central opening 114.

The annular air bladder 112 will continue to urge the medical instruments, if it moves in a side to side manner, back toward the center of the cannula passage.

What is claimed is as follows:

1. A seal assembly for use with a cannula, which comprises:

a seal housing defining a central longitudinal axis and a central opening therethrough for reception of an elongated instrument, the seal housing having internal upper and lower housing surfaces defining an annulus therebetween adjacent the central opening; and a monolithic universal seal mounted within the seal housing, the monolithic universal seal including an outer ring fixedly mounted to the seal housing, an inner ring disposed within the annulus, and an inner seal portion extending radially inwardly from the inner ring and defining an aperture for sealed reception of the elongated instrument, the inner ring being deformable and having upper and lower contacting surfaces for contacting respective upper and lower housing surfaces defining the annulus, the inner ring being adapted for radial movement within the annulus and the upper and lower contacting surfaces being adapted to be deformed upon offset insertion of the elongated instrument within the central opening of the seal housing thereby substantially preserving a seal about the elongated instrument disposed within the aperture of the inner seal portion.

2. The seal assembly according to claim 1, wherein the monolithic seal includes a biasing portion disposed between the outer and inner rings for normally biasing the inner seal portion to a position wherein the aperture is in general longitudinal alignment with the opening of the seal housing.

3. The seal assembly according to claim 2, wherein the biasing portion includes a bellows.

4. The seal assembly according to claim 1 wherein the inner ring of the monolithic seal is dimensioned and configured such that the upper and lower contacting surfaces of the inner ring are in sliding contacting relation with the respective upper and lower housing surfaces during radial movement of the inner ring.

5. A seal assembly for use with a cannula, which comprises:

a seal housing defining a central longitudinal axis and a central opening therethrough for reception of an elongated instrument, the seal housing having internal upper and lower housing surfaces defining an annulus therebetween adjacent the central opening; and a monolithic universal seal mounted within the seal housing, the monolithic universal seal including an outer ring fixedly mounted to the seal housing, an inner ring disposed within the annulus, and an inner seal portion extending radially inwardly from the inner ring and defining an aperture for sealed reception of the elongated instrument, the inner ring being deformable and having upper and lower contacting surfaces for contacting respective upper and lower housing surfaces defining the annulus, the inner ring being adapted for radial movement within the annulus upon offset insertion of the elongated instrument within the central opening of the seal housing thereby substantially preserving a seal about the elongated instrument disposed within the aperture of the inner seal portion, the universal seal including a biasing portion disposed between the inner and outer rings for normally biasing the inner seal portion to a position wherein the aperture is in general longitudinal alignment with the opening of the seal housing, the biasing portion including a flexible bladder inflatable with a fluid media.

6. The seal assembly according to claim 4, wherein the flexible bladder is inflated with air.

7. A seal assembly for use with a cannula, which comprises:

a seal housing defining a central longitudinal axis and a central opening therethrough for permitting passage of an elongated object;

a universal seal mounted within the seal housing, the universal seal including an outer portion and an inner seal portion extending radially inwardly from the outer portion, the inner seal portion defining an aperture for sealed reception of the elongated object, the outer portion including a self contained, closed, and inflated membrane adapted to bias the inner seal portion to a position where the aperture is in general longitudinal alignment with the central opening of the seal housing while permitting the aperture of the inner seal portion to radially move with respect to the longitudinal axis upon offset manipulation of the elongated object.

8. The seal assembly according to claim 7, wherein the inner seal portion includes opposed substantially planar surface portions having the aperture defined therein.

9. The seal assembly according to claim 8, wherein the inner seal portion is a generally flat seal.

10. The seal assembly according to claim 7, wherein the inflated membrane is at least partially filled with air.

11. The seal assembly according to claim 7 wherein the outer portion of the universal seal includes an outer ring, the outer ring connected to the seal housing.

12. The seal assembly according to claim 11 wherein the inflatable membrane is connected to the outer ring of the universal seal.

13. A seal assembly for use with a cannula, which comprises:

a seal housing defining a central longitudinal axis and a central opening therethrough for permitting passage of an elongated object;

a universal seal mounted within the seal housing, the universal seal including an outer portion and an inner seal portion extending radially inwardly from the outer portion, the inner seal portion defining a generally conical seal having an aperture for sealed reception of the elongated object, the outer portion including an inflatable membrane adapted to bias the inner seal portion to a position where the aperture is in general longitudinal alignment with the central opening of the seal housing while permitting the aperture of the inner seal portion to radially move with respect to the longitudinal axis upon offset manipulation of the elongated object.

14. A seal assembly for use with a cannula, which comprises:

a seal housing defining a central longitudinal axis and a central opening therethrough for permitting passage of an elongated object;

a universal seal mounted within the seal housing, the universal seal including an outer portion and an inner seal portion extending radially inwardly from the outer portion, the inner seal portion includes first and second seal membranes, each seal membrane having an aperture for sealed reception of the elongated object, the outer portion including an inflatable membrane adapted to bias the inner seal portion to a position where the apertures are in general longitudinal alignment with the central opening of the seal housing while permitting the apertures of the inner seal portion to radially move with respect to the longitudinal axis upon offset manipulation of the elongated object.

15. A seal assembly for use with an access device, which comprises:

a seal housing having internal opposed housing surfaces defining a chamber therebetween, the seal housing defining a longitudinal opening for passage of an instrument; and a seal within the chamber of the seal housing, the seal including a peripheral portion fixedly mounted to the seal housing, an inner ring and an inner seal extending radially inwardly from the inner ring and defining an aperture for receiving the instrument in sealing relation therewith, the inner ring having opposed elastomeric surfaces in sliding contacting relation with the opposed housing surfaces, the inner ring adapted to radially move within the chamber during manipulation of the instrument and the opposed elastomeric surfaces being deformable to thereby provide a biasing force to the instrument to bias the instrument in general alignment with the longitudinal opening of the seal housing.

16. A method for sealing an instrument within an access device, comprising the steps of:

providing a seal assembly for use with the access device, the seal assembly including a seal housing defining a longitudinal opening for passage of an instrument and a seal within a chamber of the seal housing, the seal including a peripheral portion mounted with respect to the seal housing, an inner ring and an inner seal extending radially inwardly from the inner ring and defining an aperture for receiving the instrument in sealing relation therewith;

positioning the instrument within the longitudinal opening of the seal housing and advancing the instrument through the aperture of the inner seal whereby the material defining the aperture engages the instrument in substantial sealing relation therewith; and manipulating the instrument to radially move the inner ring within the chamber of the seal housing whereby outer surfaces of the inner ring contact the seal housing and deform to provide a biasing force to the instrument to bias the instrument in general alignment with the longitudinal opening of the seal housing.

17. The method according to claim 16 wherein, during the step of manipulating, the material defining the aperture of the inner seal maintains the substantial sealing relation with the instrument.

18. The method according to claim 17 wherein the seal includes a biasing portion defined between the peripheral portion and the inner ring and wherein during the step of manipulating the biasing portion biases the inner seal to a position wherein the aperture of the inner seal is in general alignment with the longitudinal opening of the seal housing.

19. The method according to claim 18 wherein the biasing portion includes a bellows structure and wherein, during the step of manipulating, the bellows structure flexes so as to urge the instrument in general longitudinal alignment with the longitudinal opening of the seal housing.

20. The method according to claim 18 wherein the biasing portion includes a flexible bladder inflatable with a fluid media and wherein, during the step of manipulating, the flexible bladder flexes so as to urge the instrument in general longitudinal alignment with the longitudinal opening of the seal housing.

21. The method according to claim 17 wherein the peripheral portion of the seal includes an outer ring and further including the step of securing the outer ring within the seal housing.

* * * * *